US008636658B2

(12) United States Patent
Su et al.

(10) Patent No.: US 8,636,658 B2
(45) Date of Patent: Jan. 28, 2014

(54) SURGICAL RETRACTOR HAVING A LIGHTING UNIT

(75) Inventors: Ying-Chieh Su, Tainan (TW); Chao-Kun Chen, Tainan (TW); Yao Fong, Tainan (TW)

(73) Assignee: Chi Mei Medical Center, Tainan (TW)

( * ) Notice: Subject to any disclaimer, the term of this patent is extended or adjusted under 35 U.S.C. 154(b) by 0 days.

(21) Appl. No.: 13/545,507

(22) Filed: Jul. 10, 2012

(65) Prior Publication Data
US 2013/0018230 A1   Jan. 17, 2013

(30) Foreign Application Priority Data

Jul. 13, 2011   (TW) .............................. 100124770 A

(51) Int. Cl.
*A61B 1/32* (2006.01)
(52) U.S. Cl.
USPC ............ 600/245; 600/201; 600/208; 600/212

(58) Field of Classification Search
USPC .................................. 600/184–200, 201–246
See application file for complete search history.

(56) References Cited

U.S. PATENT DOCUMENTS

| 2008/0097163 | A1* | 4/2008 | Butler et al. ................. 600/208 |
| 2008/0103366 | A1* | 5/2008 | Banchieri et al. ............ 600/208 |

* cited by examiner

*Primary Examiner* — Mary Hoffman
*Assistant Examiner* — Christina NegrelliRodriguez
(74) *Attorney, Agent, or Firm* — Steven B. Phillips; Moore & Van Allen PLLC

(57) ABSTRACT

A surgical retractor includes an outer ring unit, a tubular retraction membrane made of a resilient material and including an inner surface defining a passageway, and a lighting unit. The tubular retraction membrane has an outer tubular end connected to the outer ring unit and rollable about the outer ring unit. The lighting unit is connected to an inner tubular end of the retraction membrane and includes a light-emitting ring, and a heat-dissipation ring in contact with the light-emitting ring.

7 Claims, 4 Drawing Sheets

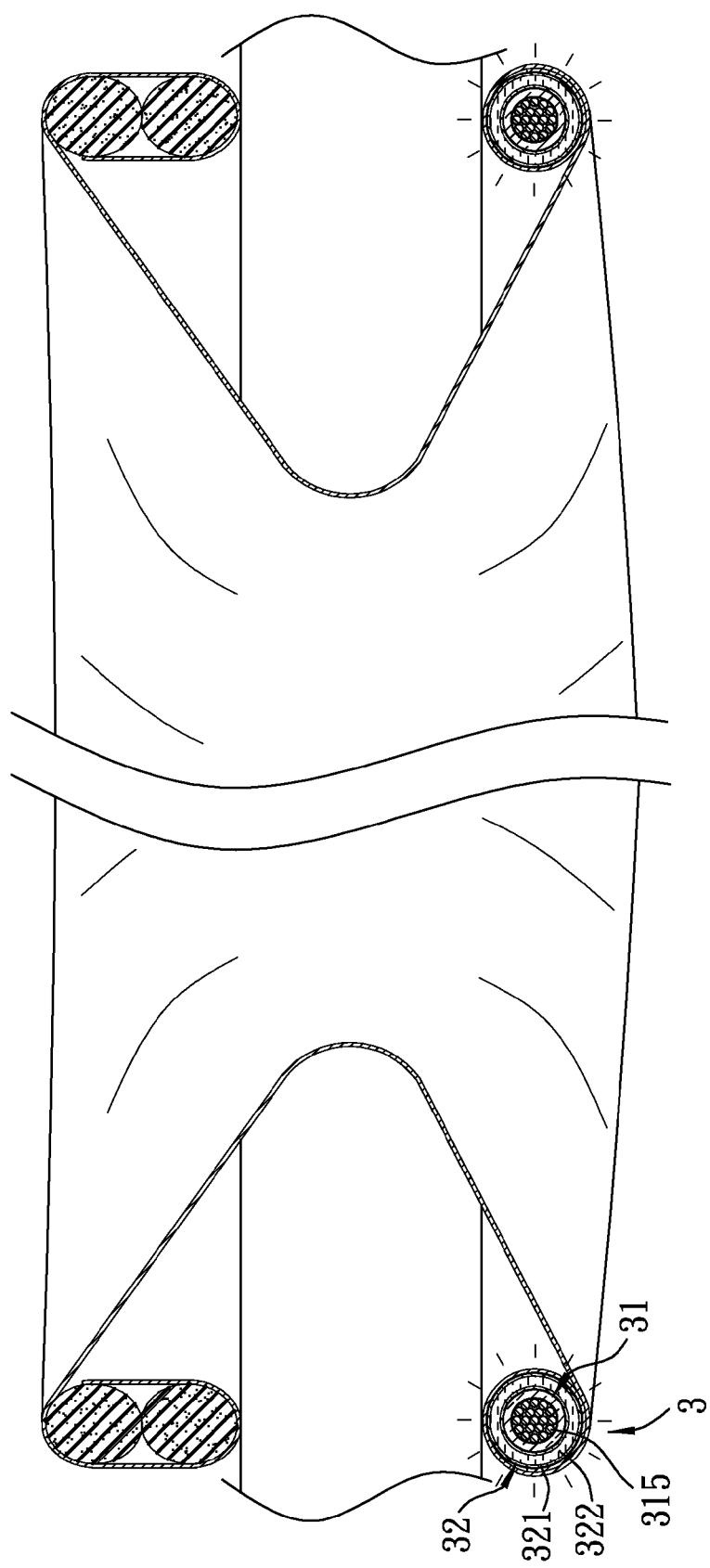

SURGICAL RETRACTOR HAVING A LIGHTING UNIT

CROSS REFERENCE TO RELATED APPLICATION

This application claims priority of Taiwanese application no. 100124770 filed on Jul. 13, 2011.

BACKGROUND OF THE INVENTION

1. Field of the Invention

The invention relates to a surgical retractor, and more particularly to a surgical retractor incorporating a lighting unit.

2. Description of the Related Art

It is well known to use a surgical retractor for retracting an incision in an abdominal wall and for exposure of an interior part of a patient's body during a laparotomy or thoracotomy operation. The commonly used retractors include manually and mechanically operated retractors, such as a plain retractor, a rake retractor, a self-retraining retractor, etc. Generally, conventional retractors require a relatively complicated retraction procedure in use, and are composed of metal parts that are likely to exert uneven pressure and cause injury to the sides of an incision and that may damage other surgical instruments upon frictioning and impacting during surgery.

Illumination is an essential means for inspection of an interior body part within an incision during surgery. Illumination effects provided by traditional external illumination equipment are usually limited by the size of the incision, the position of the surgeon, and the manipulation of surgical tools. An internal illumination device is usually provided in an endoscopic surgery to illuminate a deep body cavity of the patient. Nevertheless, the internal illumination device tends to occupy an additional surgical port and interfere with the manipulation of surgical instruments used during surgery. The internal illumination device is therefore not practical in open wound surgery.

SUMMARY OF THE INVENTION

One object of the present invention is to provide a surgical retractor that incorporates a lighting unit and that is convenient and safe for use.

Accordingly, the present invention provides a surgical retractor which comprises an outer ring unit, a tubular retraction membrane made of a resilient material and including an inner surface defining a passageway, and a lighting unit. The tubular retraction membrane includes opposite inner and outer tubular ends. The outer tubular end is connected to the outer ring unit and can be rolled about the outer ring unit. The lighting unit is attached to the inner tubular end, and includes a light-emitting ring, and a heat-dissipation ring in contact with the light-emitting ring.

BRIEF DESCRIPTION OF THE DRAWINGS

Other features and advantages of the present invention will become apparent in the following detailed description of the preferred embodiments with reference to the accompanying drawings, of which:

FIG. 4 is a side sectional view illustrating the second preferred embodiment in use.

DETAILED DESCRIPTION OF THE PREFERRED EMBODIMENTS

Figure 1:
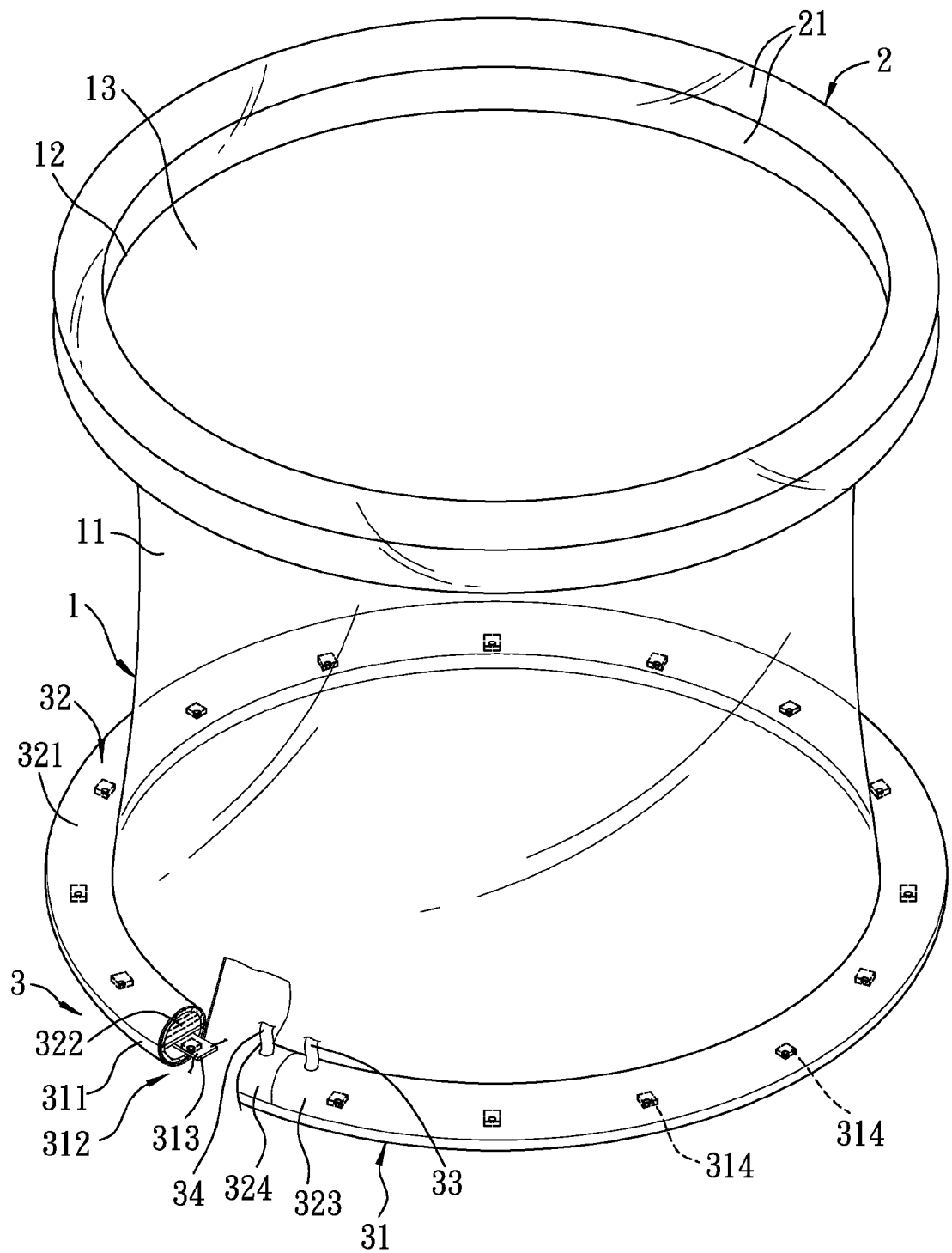
FIG. 1 is a perspective view of the first preferred embodiment of a surgical retractor according to the present invention.

Before the present invention is described in greater detail with reference to the accompanying preferred embodiments, it should be noted herein that like elements are denoted by the same reference numerals throughout the disclosure.

Figure 2:
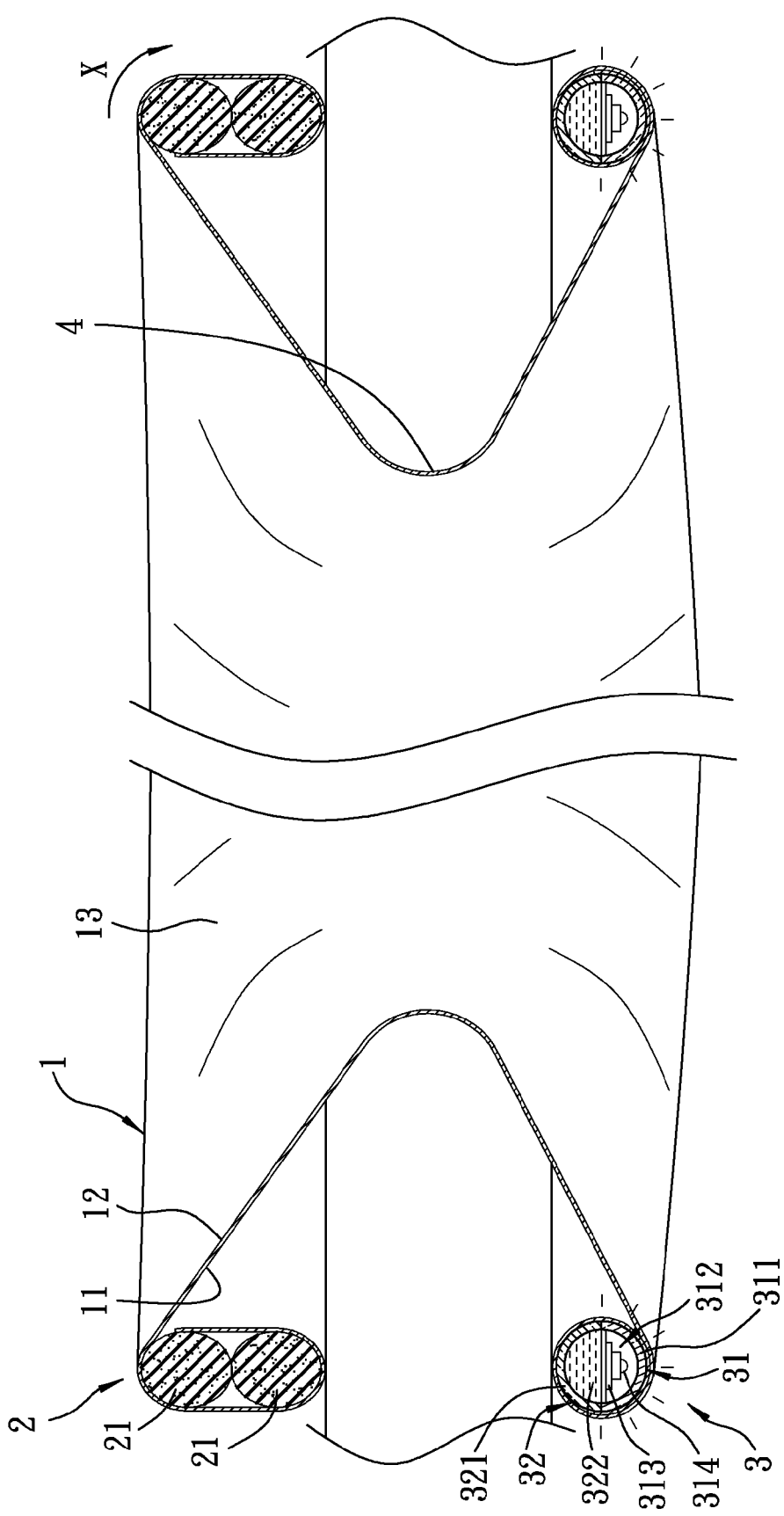
FIG. 2 is a side sectional view illustrating the first preferred embodiment in use.

Referring to FIGS. 1 and 2, there is shown the first preferred embodiment of a surgical retractor according to this invention, which can be used as a surgical laparotomy retractor, and which includes a tubular retraction membrane 1 made of a resilient material, an outer ring unit 2 and an inner ring unit or lighting unit 3.

The tubular retraction membrane 1 is used for insertion into and for retraction of an incision 4 in a patient's abdominal wall, and includes an inner tubular end to extend into the incision 4 and an outer tubular end to be disposed outside the incision 4. The tubular retraction membrane 1, when inserted into the incision 4, retracts the incision 4 by uniformly applying a retraction force in all directions of 360 degrees to the tissue around the incision 4. Therefore, an outer peripheral surface 11 of the tubular retraction membrane 1 is in intimate contact with the sides of the incision 4. The inner surface of the tubular retraction membrane 1 defines a passageway 13. In this embodiment, the tubular retraction membrane 1 is made of a rubber material.

The outer ring unit 2 is connected to the outer tubular end of the tubular retraction membrane 1 and can be rolled into the outer tubular end of the tubular retraction membrane 1 when the outer ring unit 2 is turned inside out to fold the outer tubular end around the outer ring unit 2 and to stretch the tubular retraction membrane 1. The incision 4 can thus be retracted and fixed into a predetermined size and shape to expose an interior part of the patient's body for a surgical operation. In this embodiment, the outer ring unit 2 includes two axially stacked plastic rings 21 each having an oval cross section. A maximum width of the oval cross section of each of the rings 21 is disposed along an axial direction of the outer ring unit 2.

The lighting unit 3 is connected to the inner tubular end, has a ring shape, and includes a light-emitting ring 31, and a heat-dissipation ring 32 in contact with the light-emitting ring 31.

The light-emitting ring 31 includes a resilient ring-shaped transparent tube body 311 having a semi-circular cross section, and a light source 312 disposed within the transparent tube body 311 and disposed along an angular direction thereof. In this embodiment, the light source 312 is arranged to include a ring-shaped flexible circuit board 313, and a plurality of light-emitting diodes 314 mounted on the flexible circuit board 313 in an annularly spaced apart position. However, any other suitable arrangement capable of emitting light may be used for the light source 312.

The heat-dissipation ring 32 includes a looped tube body 321 having a semi-circular cross section and stacked on and complementing with the transparent tube body 311 of the light-emitting ring 31 to form a circular cross section, and a heat-absorbing fluid 322 filled in the looped tube body 321. In this embodiment, the looped tube body 321 is made of a resilient translucent material, and the heat-absorbing fluid 322 is water. However, the present invention should not be limited only thereto. The looped tube body 321 has two juxtaposed closed ends 323, 324 connected to each other, but not fluidly communicated with each other. The heat-absorbing fluid 322 is injected into the looped tube body 321 through the closed end 323 and is discharged from the closed end 324.

The lighting unit 3 further has an inlet tube 33 connected to the closed end 323 for inletting the heat-absorbing fluid 322, and an outlet tube 34 connected to the other closed end 324 for outletting the heat-absorbing fluid 322.

The incision 4 is cut in the abdominal wall of the patient, and the tubular retraction membrane 1 is inserted into the incision 4 with the outer ring unit 2 disposed outside the incision 4 and the lighting unit 3 disposed inside the patient's body. When the outer ring unit 2 is gripped by a surgeon and is turned inside out as shown by arrow (X), the outer tubular end of the tubular retraction membrane 1 is folded outward and is rolled about the outer ring unit 2. Thus, the tubular retraction membrane 1 is expanded and stretched tightly outward to retract the incision 4 so that a substantially circular shaped incision opening with a predetermined size is formed. At this state, since the diameters of the outer ring unit 2 and the lighting unit 3 are larger than that of the incision 4, the tubular retraction membrane 1 converges from its inner and outer tubular ends to its intermediate part contacting the sides of the incision 4.

When an electric power is supplied to the lighting unit 3, the light source 312 is activated to emit light through the transparent tube body 311, forming an annular illumination ring that provides a wide range of illuminated region. At the same time, the heat-absorbing fluid 322 is arranged to constantly flow through the heat-dissipation ring 32 and to absorb the heat generated by the light source 312 so that a surgical operation can be performed smoothly under good heat-dissipated conditions.

In the present invention, the tubular retraction membrane 1 can exert a uniform force in all directions of 360 degrees to the tissue around the incision 4, and has an annular wall to contact against the exposed edges of the incision 4 and to retract the incision 4 to form a substantially circular incision opening. Therefore, the tubular retraction membrane 1 can protect the exposed edges of the incision 4 from being injured by surgical tools used during surgery and from being infected and contaminated. Moreover, since the lighting unit 3 can provide a wide range of illuminated region inside the patient's body, the rate of relying on external or internal illumination equipment for surgery may be lowered. Therefore, the surgical retractor of the present invention is convenient and safe for use.

Figure 3:
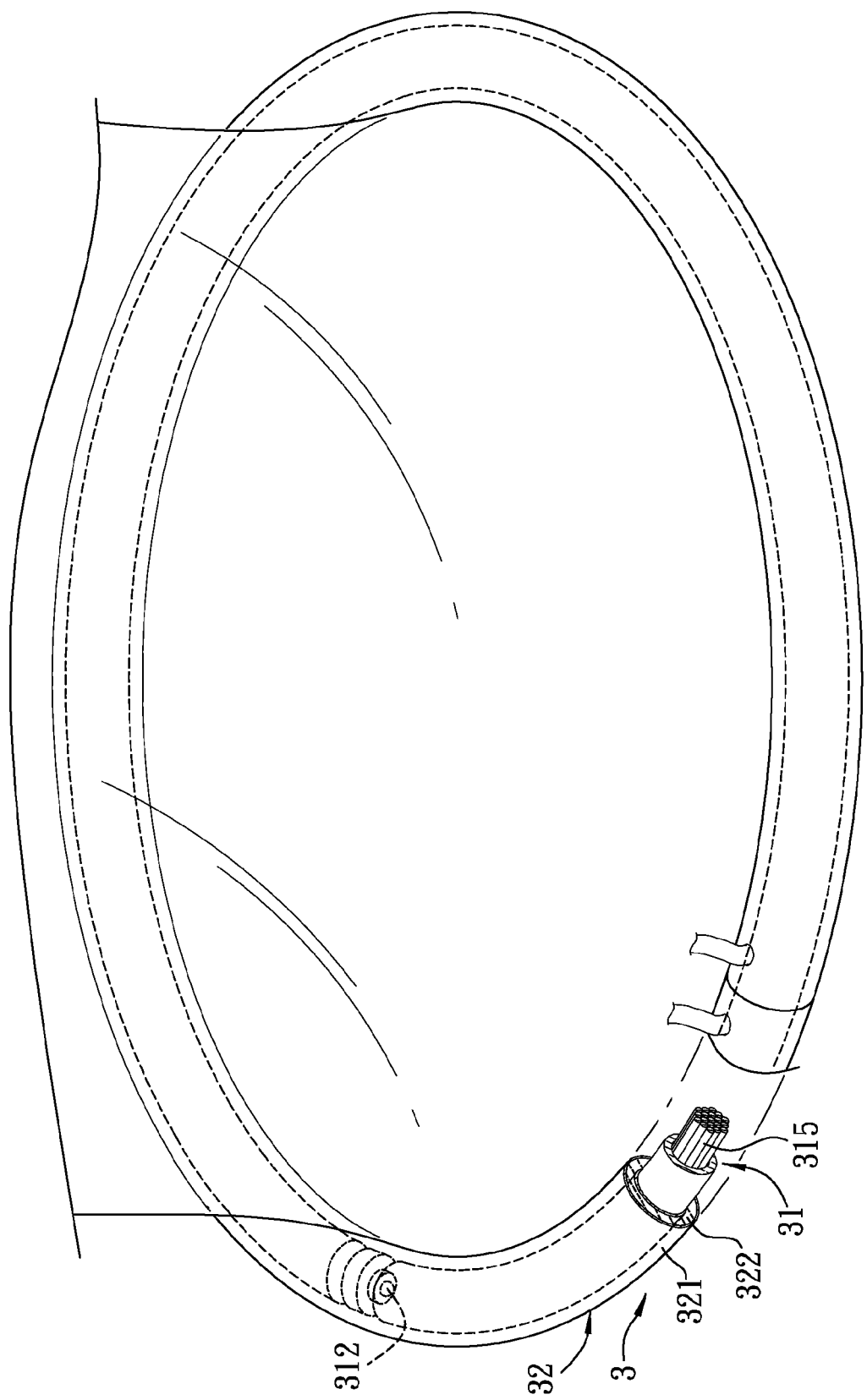
FIG. 3 is a perspective view of the second preferred embodiment of a surgical retractor according to the present invention.

Referring to FIGS. 3 and 4, the second preferred embodiment of this invention differs from the first preferred embodiment in that, the light-emitting ring 31 of the lighting unit 3 includes an optical fiber light guide 315, which is formed as an open loop, and a light source 312 disposed at one open end of the optical fiber light guide 315. In this embodiment, the light source 312 is a light-emitting diode.

The looped tube body 321 of the heat-dissipation ring 32 is made of a transparent material and has a circular cross section. The looped tube body 321 encloses the optical fiber light guide 315 of the light-emitting ring 31, and the heat-absorbing fluid 322 disposed inside the looped tube body 321 and around the optical fiber light guide 315.

When the light source 312 is activated, the optical fiber light guide 315 will emit light radially in all directions through the looped tube body 321 of the heat-dissipation ring 32. In comparison with the first preferred embodiment, the second preferred embodiment can provide a better illumination effect or larger illuminated region.

While the present invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A surgical retractor comprising:
    an outer ring unit;
    a tubular retraction membrane made of a resilient material, and including an inner surface defining a passageway, and opposite inner and outer tubular ends, said outer tubular end being connected to said outer ring unit, wherein said outer tubular end can be rolled about said outer ring unit; and a lighting unit attached to said inner tubular end and including a light-emitting ring, and a heat-dissipation ring in contact with said light-emitting ring, wherein said light-emitting ring includes a ring-shaped transparent tube body, and a light source disposed within said transparent tube body, and
    wherein said heat-dissipation ring includes a looped tube body stacked on said transparent tube body of said light-emitting ring, and a heat-absorbing fluid filled in said looped tube body.

2. The surgical retractor of claim 1, wherein said transparent tube body of said light-emitting ring and said looped tube body of said heat-dissipation ring are semi-circular in cross section and complement each other to form a circular cross section.

3. A surgical retractor comprising:
    an outer ring unit;
    a tubular retraction membrane made of a resilient material, and including an inner surface defining a passageway, and opposite inner and outer tubular ends, said outer tubular end being connected to said outer ring unit, wherein said outer tubular end can be rolled about said outer ring units; and
    a lighting unit attached to said inner tubular end and including a light-emitting ring, and a heat-dissipation ring in contact with said light-emitting ring,
    wherein said heat-dissipation ring includes a looped tube body that has two closed ends juxtaposed to each other, an inlet tube connected to one of said closed ends for inletting said heat-absorbing fluid, and an outlet tube connected to the other one of said closed ends for outletting said heat-absorbing fluid.

4. The surgical retractor of claim 3, wherein said outer ring unit includes two rings, which are stacked axially on each other.

5. The surgical retractor of claim 4, wherein each of said rings of said outer ring unit has a substantially elliptical cross section that has a maximum width disposed in an axial direction of said outer ring unit.

6. A surgical retractor comprising:
    an outer ring unit;
    a tubular retraction membrane made of a resilient material, and including an inner surface defining a passageway, and opposite inner and outer tubular ends, said outer tubular end being connected to said outer ring unit, wherein said outer tubular end can be rolled about said outer ring units; and
    a lighting unit attached to said inner tubular end and including a light-emitting ring, and a heat-dissipation ring in contact with said light-emitting ring, wherein said light-emitting ring includes an optical fiber light guide, and a light source disposed at one end of said optical fiber light guide, wherein said heat-dissipation ring includes a looped tube body made of a transparent material and enclosing said optical fiber light guide, and a heat-absorbing fluid disposed inside said looped tube body and around said optical fiber light guide.

7. The surgical retractor of claim 6, wherein said light-emitting ring includes a light-emitting diode.

* * * * *

UNITED STATES PATENT AND TRADEMARK OFFICE
CERTIFICATE OF CORRECTION

| | | |
|---|---|---|
| PATENT NO. | : 8,636,658 B2 | Page 1 of 1 |
| APPLICATION NO. | : 13/545507 | |
| DATED | : January 28, 2014 | |
| INVENTOR(S) | : Ying-Chieh Su, Chao-Kun Chen and Yao Fong | |

It is certified that error appears in the above-identified patent and that said Letters Patent is hereby corrected as shown below:

On the Title page, please change (75) Inventors to:

Ying-Chieh Su, Tainan City (TW); Chao-Kun Chen, Tainan City (TW); Yao Fong, Tainan City (TW)

On the Title page, please change (73) Assignee to:

Chi Mei Medical Center, Tainan City (TW)

Signed and Sealed this
Twenty-ninth Day of April, 2014

Michelle K. Lee
*Deputy Director of the United States Patent and Trademark Office*